(12) United States Patent
Resch-Genger et al.

(10) Patent No.: US 7,919,744 B2
(45) Date of Patent: Apr. 5, 2011

(54) OPTICAL STANDARD FOR THE CALIBRATION AND CHARACTERIZATION OF OPTICAL MEASURING DEVICES

(75) Inventors: Ute Resch-Genger, Berlin (DE); Katrin Hoffmann, Berlin (DE); Thomas Behnke, Berlin (DE); Christian Wuerth, Berlin (DE)

(73) Assignee: Bam Bundesanstalt fuer Materialforschung und Pruefung, Berlin (DE)

( * ) Notice: Subject to any disclaimer, the term of this patent is extended or adjusted under 35 U.S.C. 154(b) by 9 days.

(21) Appl. No.: 12/505,660

(22) Filed: Jul. 20, 2009

(65) Prior Publication Data

US 2010/0243876 A1 Sep. 30, 2010

(30) Foreign Application Priority Data

Mar. 24, 2009 (EP) .................................. 09156073

(51) Int. Cl.
*G01D 18/00* (2006.01)
(52) U.S. Cl. .................................................. 250/252.1
(58) Field of Classification Search ................. 250/252.1
See application file for complete search history.

(56) References Cited

U.S. PATENT DOCUMENTS

| 5,616,823 | A | * | 4/1997 | Lattimore | .............. | 73/1.03 |
| 7,480,042 | B1 | | 1/2009 | Phillips et al. | | |
| 2008/0314114 | A1 | | 12/2008 | Feke et al. | | |

FOREIGN PATENT DOCUMENTS

| DE | 102004044717 A1 | 3/2006 |
| DE | 102008040513 A1 | 1/2010 |
| EP | 1857790 A2 | 11/2007 |

OTHER PUBLICATIONS

J.A.Gardecki et al.; Set of Secondary Emission Standards for Calibration of the Spectral Responsivity in Emission Spectroscopy; Applied Spectroscopy, 1998, V. 52, P. 1179-1189.
S.A. Tucker et al.; Effect of K2Cr2O7 on Fluorescence Emission Intensities of Quinine Sulfate; J. Chem Ed. 1992; 69 (1), A8-A12.
R. Giebeler et al.; Performance Validation for Microplate Fluorimeters; J. Fluoresc. 2005; 15(3); 363-375.
I.T. Young; The Use of Digital Image Processing Techniques for the Calibration of Quantitative Microscopes; SPIE 1983; 387, 326-335.

* cited by examiner

*Primary Examiner* — David P Porta
*Assistant Examiner* — Kiho Kim
(74) *Attorney, Agent, or Firm* — Harness, Dickey & Pierce, PLC

(57) ABSTRACT

The invention relates to an optical standard (10) for the calibration or characterization of optical measuring devices and as a reference system for intensities and intensity measurements. The standard (10) according to the invention, constructed sandwich-like, comprises a combination of at least two layer-like optical standard modules (12) having defined optical properties, joinable or joined together plane-parallel, wherein the standard modules (12) in each instance differ from each other by at least one optical property, namely, by their absorption, emission, scatter and/or reflection properties, and the standard modules (12) are made so that they enter into physical interaction with electromagnetic radiation striking one of their two principal surfaces (12.1).

Figure 1A:
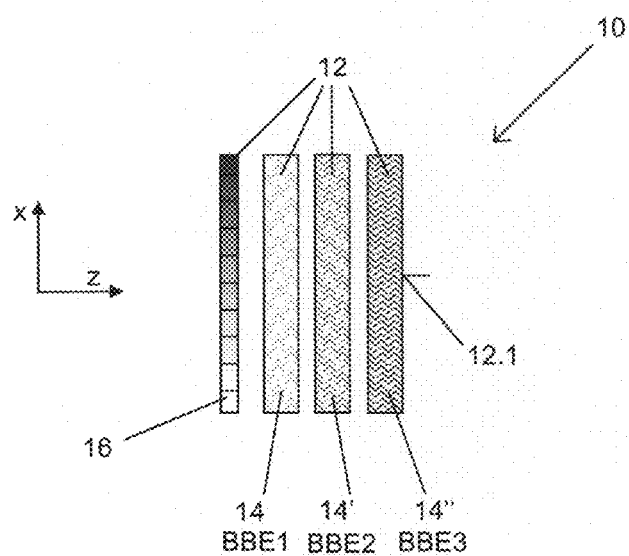

18 Claims, 10 Drawing Sheets
(2 of 10 Drawing Sheet(s) Filed in Color)

OPTICAL STANDARD FOR THE CALIBRATION AND CHARACTERIZATION OF OPTICAL MEASURING DEVICES

FIELD

The invention relates to an optical standard for the calibration or characterization of optical measuring devices, in particular luminescence-measuring instruments, and their uses.

BACKGROUND

The use of optical measuring devices, for instance in research and development or in industrial quality control, presents a great many problems, which require regular calibration and characterization of optical measuring devices. These are to be illustrated by way of the example of luminescence-measuring instruments, where reference systems for the measurement of intensities are additionally required.

Spectral Fluorescence and Emission Standards for Emission Correction

Every luminescence-measuring technique supplies measurement data that are composed of analyte- and instrument-specific contributions. These reflect the wavelength dependence of the light source(s) and optical structural elements contained in the excitation and emission channel of the instrument, as well as the spectral sensitivity of the detection systems used. The comparability of luminescence data over instrument and laboratory limits, the determination of instrument aging, the restorability (EN ISO/IEC 17025) of luminescence data and the optimization of luminescence methods require the determination of these instrument-specific effects in order to correct measured spectra of an analyte and to obtain the pure analyte-specific contributions. This also applies to measuring methods that compare the emission of luminophores with spectrally unlike emission spectra, such as for example the determination of fluorescence quantum yields, and for emission measurements at various excitation wavelengths. These instrument-specific effects are identified by the determination of what are called emission and excitation correction functions, which include the wavelength dependence and polarization dependence of the spectral sensitivity of the detection channels used (emission correction) and the wavelength dependence and polarization dependence of spectral illuminance at the sampling location and the intensity of excitation light (excitation correction).

Simple and restorable calibration of luminescence-measuring systems can be effected with certified physical transfer standards, that is, with a certified radiation-intensity-per-unit-area standard, a standard lamp (typically for the emission channel) and/or a certified receiver standard (typically for the excitation channel). Alternatively, chemical transfer- and so-called fluorescence standards with (ideally certified) spectrally corrected, that is, instrument-independent emission and/or excitation spectra can be used. The restorable and ideally certified (physical or chemical) transfer standards should insofar as possible be measurable under conditions identical to those of typical samples (for example in like sample containers/formats, with like polarizer settings, filters and reducers, as well as like settings for monochromator slot width, photomultiplier voltage, sampling interval and integration time or scanning speed) and be suitable for as many as possible different types of instruments, formats and measurement geometries, and cover a broad spectral region, typically UV/vis, vis/NIR and/or UV/vis/NIR. With increasing use of the NIR spectral region for a great variety of fluorescence applications (for example, optical imaging; $1^{st}$ diagnostic window of about 650 to 900 nm and $2^{nd}$ diagnostic window of about 1300 to 1500 nm), standards for the NIR spectral region are becoming increasingly important.

A prerequisite for suitability as a chemical transfer standard and reference material is problem-specific dye selection. This implies for example broad, smooth and unstructured emission spectra in the case of spectral emission standards and broad, smooth and unstructured absorption and excitation spectra in the case of excitation standards. For chemical transfer standards, their corrected emission and/or excitation spectra and preferably measurement uncertainty must in addition be known.

The restorable calibration of luminescence-measuring systems in the UV/vis/NIR spectral region requires the combination of a plurality of chromophores with (ideally certified) corrected fluorescence spectra which are adapted to each other. This includes, in particular, in addition to broad, rising as flatly as possible, unstructured bands of points of intersection of adjacent spectra at sufficiently high fluorescence intensities, so as to ensure linking of individual correction curves to a total correction function with as little as possible measurement uncertainty. There are only a few examples of the application of chromophore combinations to the determination of emission correction in the UV/vis/NIR spectral region. Chromophore-containing polymer films (NIST, certified emission spectra), a combination of the emission standard quinine sulfate dihydrate (SRM 936a) with cell-like chromophore-doped glasses and emission standard solutions are examples of emission standard combinations (for example, J. A. Gardecki, M. Maroncelli, Appl. Spectrosc. 1998, 52, 1179). In addition, chromophore-containing polymethyl methacrylate (PMMA) blocks in cell form are available as emission standards (Starna, Optiglass) and standard solutions (Invitrogen, formerly Molecular Probes). A kit of spectral fluorescence standards, which permits emission and absorption correction in a broad spectral region, is disclosed in DE 10 2004 044,717 A. According to the later application DE 10 2008 040,513.2, the covered spectral region is capable of being broadened in the NIR region by combination with a long wave-emitting cyanine compound as the spectral fluorescence standard.

In addition, statistical methods for linking the correction functions obtained for the individual emission standards to a total correction function are [disclosed] in the Gardecki source and in DE 10 2004 044,717 A, mentioned above.

All known standard combinations always present a combination of unique standards, each standard often having to be excited at a different excitation wavelength for emission. This means that each component of a standard set must be measured separately, and each measurement supplies an emission correction curve for a limited spectral region of at most 150 to 200 nm ($\Delta\lambda$ in the vis region) in the case of chromophore-based standards (for example quinine sulfate), which corresponds to the emission region of the respective standard and chromophore. These standard-specific correction curves must be combined in a subsequent step by evaluated mathematical procedures into a total correction curve, so as to cover a broad spectral region. Adaptation of the emission intensities of various standards to each other, which is necessary in for example the case of greatly varying extinction coefficients and fluorescence quantum yields as well as on the instrument side in the case of greatly varying spectral sensitivities, can only be effected by the adaptation of chromophore concentrations for liquid standards. In the case of solid standards, adaptation typically is no longer possible.

Standards for the Testing of Instrument Performance and Long-Term Stability of Instruments (Day-To-Day Intensity Standards)

Standards for the testing of instrument performance and long-term stability of instruments (so-called day-to-day intensity standards) are necessary in order for example to identify instrument drift caused by the aging of optical and optico-electronic structural parts and to permit comparability of measurements of relative fluorescence intensities carried out on different days. The availability of such standards is, in addition, very important for the regular performance of instrument tests and examinations necessary in connection with laboratory accreditations per ISO 17025. The most frequent and at present single established test for testing instrument performance and long-term instrument stability is the so-called Raman test. For this, non-fluorescent ultrapure water is irradiated at 350 nm, and the intensity of Raman scattering at 397 nm is measured. This test is only suitable for the UV spectral region.

In addition, it is known that variation of the intensity of emitters may be realized by their combination with an absorber. For this, quinine sulfate emitting broadband in the vis spectral region, for example, has been combined with a broadband-absorbing absorber (S. A. Tucker et al., J. Chem. Ed. 1992, 69(1), A8-A12) or a comparably narrow band-emitting fluorophore with a narrow-band absorber (R. Giebeler et al., J. Fluoresc. 2005, 15(3), 363-375).

Intensity Standards

Fundamentally, every luminescence technique supplies only relative intensities, if all photons emitted after chromophore excitation are not detected, as is the case, for example. in Ulbricht ball-measuring systems. For a quantification of intensity measurements, in most cases, either a correlation with the concentration of the emitter to be quantified is necessary (for example, by plotting a calibration straight line) or the use of an emitting reference system, i.e., an intensity standard. This may be by luminescence methods, for example fluorescence quantum yield standards (typically dye solutions of known fluorescence quanta yield) as well as calibration slides (microarray technology) or dye-labeled fluorescing particles, as in the case of flow cytometry, in which the emission intensity of the particles is previously quantified by comparing fluorescence measurements with the fluorophores used in the form of MESF units (measurable equivalents of soluble fluorophores). Another approach, derived from fluorescence microscopy, uses one or more fluorescing reference surfaces, where in as identical as possible a microenvironment a like fluorophore is used for the standard that is also to be quantified, so as to guarantee as similar as possible emission properties of sample and standard. The principle of signal referencing (signal ratioing) is common in fluorescence sensory analysis. Signal referencing can be realized in that the measured target-sensitive relative fluorescence intensity of a target-sensitive monochromatically emitting sensor molecule is referred to a second dye, which emits spectrally distinctly separately from the first fluorophore and the emission intensity of which is independent of the target. Alternatively, dual emitting sensor molecules, which, in the presence of the target exhibit very strong spectral shifts of their absorption (ratioing in excitation) or emission, or FRET systems, are used for this. Systems that can be adapted by the combination of various optical components with reference to their spectral properties to the respective problem, and the intensity of which can be adjusted or even varied problem-adapted by as simple as possible means, are desirable here. The combination of a fluorescing and an absorbing component, which serves for reduction or for the structuring of emission, or a reflecting component, is known here. For example, the combination of LEDs with reducers or the combination of emitters and absorbers for the calibration of microtiter plate readout instruments (R. Giebeler et al., J. Fluoresc. 2005, 15(3), 363-375) or an LED slide for fluorescence microscopy (I. T. Young, Proc. SPIE 1983, 38, 326-335) is well known. However, only the spectral properties or the intensity of a single fluorophore are varied there.

Intensity standards, the spectral emission properties and/or emission intensity of which can be adjusted and controlled as simply as possible without varying the chemical composition or the concentration, would be desirable, for example for application as a relative reference system for the ratiometric measurement of fluorescence intensities, for the detection of instrument drift and for the quantification of intensity-based fluorescence measurements. At the present time, a standard must be specially developed and evaluated for each application or for each desired spectral behavior or emission profile.

Determination of the Linearity Region of Luminescence Detection Systems

Knowledge of the linearity region of the detection systems used is a prerequisite for the determination of emission correction functions of luminescence-measuring systems and for any quantitative luminescence analytics. In the case of common detectors like PMTs and CCD systems, this depends upon the detection wavelength. At present, there is no uniform procedure for this. Dyes that are suitable for determination of the linearity region of fluorescence detection systems are characterized in particular by as little as possible overlapping of absorption and fluorescence. This requires that, at extinctions of up to about 0.1, emission spectra (1-cm cell) still be concentration-independent. Also generally advantageous are smooth unstructured emission spectra that cover as great as possible an emission spectral region.

One method, which is based upon an emission standard (quinine sulfate dihydrate), is described in ASTM E 578-83. The excitation and emission wavelength regions for which the method can be used, however, are limited by the absorption and emission spectrum of quinine sulfate dihydrate, so that the linearity region for the entire spectral region of interest cannot be determined. In addition, integral measuring fluorescence instruments, such as, for example, filter fluorometers, many microtiter plate readout instruments and scanners for optical imaging, are limited in the selection of excitation and emission wavelengths by the excitation light sources used (laser or lamp with excitation filter) and integral detection (emission filter and detector). Further, NIST-certified fluorescin solutions (SRM 1932) and the Molecular Probes company's fluorescin solutions (Fluorescin NIST-Traceable Standard F 36915) are available. Because of the comparatively narrow absorption and emission spectrum of fluorescin, these are only usable in a narrow vis spectral region. Also known are "Rediplate Microplate Intensity Standards" (Invitrogen), consisting of a plurality of fluorophores in solutions, which are problematic because of the great overlapping of the absorption and emission spectra, and "Fluorescence Reference Standards" (MATECH), which comprise chromophore-doped solid matrices, integrated in microtiter plates, for a variety of excitation and emission wavelengths in the UV/vis spectral region and thus are only suitable for microtiter plate readout instruments. Variation of concentration and there-fore of fluorescence intensity for problem-specific adaptation by the user is not possible.

At the present time, the concentration of the fluorophore must be varied for determination of the linearity region of luminescence detection systems. In addition, only a comparatively narrow spectral region is covered per measurement and per chromophore.

A standard that permits simple and rapid determination of the linearity of the detection system [in] a broad spectral region, preferably in the entire spectral region of the instrument (multifunctional reducer), with only a few measurements and ideally with a single standard, would be desirable.

Testing of Wavelength Accuracy and Spectral Resolution

For high-resolution spectrofluorometers, atomic emission lines of gas discharge lamps, which contain mixtures of gases such as neon and mercury, are typically used, so as to cover as great as possible a spectral region. For luminescence-measuring instruments such as microtiter plate readout instruments or spectral resolving micro-scopes or spectral resolving imaging systems for optical imaging, which have a smaller resolution of typically greater than 2 nm (so-called robust measuring instruments), wavelength accuracy and spectral resolution can also be obtained with narrow-band emitting chromophores (mixtures of a variety of lanthanide ions for example, in a glass matrix) or by the combination of one or more narrow-band absorbers with one or more emitters. There are examples of the combination of a fluorophore with an absorber, which have already been described above.

Scattering and Fluorescing Standards

Generally speaking, the measurement of fluorescence in scattering systems plays a great role in biomedical applications of fluorometry. This applies in particular to fluorometric investigations on tissues by methods of optical imaging, for example for the early diagnosis of disease-specific changes on the molecular level in the spectral region of from about 650 to 900 nm and in the second diagnostic window. So-called phantoms, which consist of an NIR fluorophore localized at one or more defined sites and a solid or liquid absorbing and scattering medium, are used as standards for this. Typically, Intralipid, Liposyn or microparticles (for example, silica, PMMA, polystyrene) inserted into a liquid or solid polymer matrix are used as a scatterer. The fluorophores used for the NIR region typically are symmetrical or asymmetrical cyanine dyes, such as indocyanine Green (ICG) or IR-125, diethylthiatricarbocyanine iodide (DTTCI), and IR-140, which are characterized by structured absorption and emission bands and a great overlapping region of absorption and fluorescence. Such systems are highly susceptible to internal filter effects (reabsorption).

Scattering fluorescence standards that permit a simple combination of any emitters with scatterers having variable scattering properties and optionally also with absorbers, so as to permit simple adaptation of the spectral emission and absorption properties of the standard to the respective problem, would be very desirable.

SUMMARY

The object of the invention is to make available a variable optical standard as a "tool" for the calibration and/or characterization of optical measuring devices, the absorption, emission and/or scattering and reflection properties of which are adjustable in simple fashion in dependence on an existing calibration or characterization problem and an existing measurement geometry. The standard ideally should cover an as broadly or flexibly adjustable as possible a spectral region with variably adjustable intensity and variably adjustable spectral profile and simplify and accelerate the calibration or characterization of the measuring device.

This object is accomplished by an optical standard having the features of Claim 1. The optical standard according to the invention for the calibration or characterization of optical measuring devices comprises a combination of at least two layer-like optical standard modules, joinable or joined together substantially plane-parallel, with defined (i.e., known) optical properties. The standard modules differ from each other by at least one of their optical properties in each instance, namely, by their absorption, emission, scattering and/or reflection properties. They are made so that they enter into physical interaction with electromagnetic radiation that strikes one of their two principal surfaces (and, when the radiation is not reflected, at least partially enters the module). "Physical interaction" here means any wavelength-dependent or independent, elastic or inelastic interaction between the irradiation electromagnetic radiation and the matter of the individual optical standard modules, in particular wavelength-dependent or independent absorption, excitation of an emission, wavelength-dependent or independent scattering and reflection. In this way, a physical interaction of the irradiated light takes place with each of the optical standard modules used, due to which radiation emerging from the standard is modulated by each of the optical standard modules with reference to at least one of the said optical properties.

The sandwich-like combination of a plurality of individual optical standard modules according to the invention enables an entire spectrum emitted, transmitted, reflected and/or scattered by the standard to be represented, which with a suitable selection of components on the one hand covers a broad spectral region, in particular the UV/vis/NIR region, or a problem-specifically adapted narrow spectral region with adjustable band shape and/or intensity and thus permits calibration and/or characterization of the measuring device in this broad or problem specifically-relevant spectral region with a small number of individual measurements, if necessary with even only a single measurement. In addition, total spectra of the standard, which may be modulated virtually as desired, can be produced. At the same time, there such a total spectrum does not necessarily correspond only to the mere sum of the individual spectra of the individual modules. Rather, when this is desired, selectively mutual influencing can be produced. The modular construction permits a simple and varied combination of the modules, so that the absorption, emission (in particular luminescence) and scattering properties can be varied problem-adapted with little expense.

At the same time, the standard can be used as an external separate characterization tool or as an internal characterization tool integrated into the measuring system.

In a preferred embodiment, the optical standard modules comprise at least one chromophore-based or physical emission standard module, which upon suitable irradiated excitation radiation can be excited for the emission of a defined (wavelength-dependent) luminescence spectrum, in particular a fluorescence spectrum. In particular, a combination of a plurality of chromophore-based and/or physical emission standard modules may be used, which advantageously are adapted to each other so that their emission bands partially overlap each other, so as to cover a predetermined as broad as possible a spectral region. It is in particular preferred that a relative intensity at the overlapping wavelengths of two "adjacent" standardized emission bands amount to at least 10%, in particular to at least 20%, of the band maximum. Chromophore-based, i.e., chemical emission standard modules, comprise organic, inorganic and inorganic-organic chromophores, which may alternatively be combined with each other. In principle, however, the use of other luminescence phenomena, such as for example electroluminescence, is also possible. In particular, lamps with a broad emission spectrum or narrow emission spectrum or a spectrum consisting of a multiplicity of narrow lines, are physical emission standards. The spectrum emitted from at least one emission standard module preferably is modulated by additional standard modules, modulating comprising superimposition of absorption and/or other emission bands, cutting of the spectrum by filters, uniform intensity reduction, improvement of homogeneity of illumination, etc.

In connection with the present invention, the optical standard according to the invention preferably is designed as an emission standard, having at least one emission standard module. Here, the term "emission standard" comprises in particular spectral fluorescence standards for determination of the relative spectral sensitivity of detection systems (for which a broad unstructured spectrum is preferred) or for determination and testing of wavelength accuracy and spectral resolution (for which a structured spectrum with a plurality of as narrow as possible bands in as broad as possible a spectral region is preferred), as well as intensity standards. An intensity standard, such as, for example, a quantum yield standard, is at the same time a reference system for the measurement of relative intensities at a fixed excitation wavelength and a fixed emission wavelength or at a fixed excitation wavelength and integral over a defined emission spectral region, which with reference to its spectral properties either is adapted to the sample or should clearly differ from them spectrally. For application as a so-called day-to-day intensity standard or for determination of the linearity region of a detection system, a plurality of emission bands over as broad as possible an emission spectral region may also be advantageous.

In addition, the optical standard modules may comprise at least one absorption standard module for wavelength-dependent absorption of radiation, while here, too, a combination of a plurality of absorption standard modules may be provided. Some of the chromophores usable as chemical emission standards—since emission presumes absorption—may also be used as absorption standards. In particular possible as absorbers are all systems that can be used for selective modulation of the emission spectrum of the standard, i.e., for control of its spectral position and/or shape and/or intensity.

With particular advantage, the standard modules of the optical standards according to the invention comprise a combination of at least two, in particular at least three, emission standard modules adapted to each other and/or a combination of at east two, in particular at least three, absorption standard modules adapted to each other.

Chromophore-based (chemical) emission or absorption standards comprise in particular solutions of the chromophores in suitable solvents and chromophore-doped solid matrices, such as chromophore-doped glasses and glass ceramics or chromophore-doped organic, inorganic and inorganic-organic polymer matrices. These may be designed as volume systems, layers, films and foils of variable thickness, gels, hydrogels and particles of variable size or as printed, bonded or pressed layers of organic, inorganic-organic and inorganic phosphors, such as, for example, YAG:Cerium (pure material or thinned with a non-fluorescent additive such as, for example, barium sulfate, Teflon, polymer particles; also various particle sizes of phosphor). The chromophores or chromophore mixtures used as emission or absorption standards may then be inorganic or organic substances with narrow-band or broadband emission and absorption spectra. In connection with the present invention, here, "narrow band" means a band width at half height (full width at half height FWHH; examples given here referred to the vis spectral region) of at most 50 nm, in particular of at most 30 nm or even less. In contrast, by "broadband" is meant a bandwidth of usually more than 60 nm, in particular at least 80 nm or even about 100 nm or more. Organic dyes may have LE-like emission (for locally excited (state), i.e., emission of species found in the Franck-Condon state) or CT-like emission (for charge-transfer) or dual fluorescence. Inorganic chromophores comprise in particular transition and rare earth metal ion complexes, such as, for example, Ru(II) or Pt(II) compounds or Eu(II) or Eu(III) complexes, as well as luminescent rare earth metals, including scandium, yttrium, lanthanum and the lanthanoids (including 14 elements of atomic numbers 58 to 71), in particular cerium (Ce), europium (Eu), terbium (Tb), thulium (Tm), erbium (Er), samarium (Sm), holmium (Ho). Likewise usable are systems that exhibit particle size-dependent (as a rule continuous) absorption and narrow emission or more rarely also broad emission, such as, for example, semiconductor nanocrystals (examples of nanocrystals are, among others, classic quantum dots such as CdSe and CdTe, NIR quantum dots, such as PbS, PbSe or CdHgTe and quantum dots doped with a variety of metal ions, such as, for example, Mn(II)-doped ZnS or ZnSe or silicon particles, carbon nanotubes, quantum wires, nanorods, etc.) or metal nanoparticles. OLED materials and OLED layers are also possible. Depending upon the application, in addition to the chemical, i.e., chromophore-based systems already mentioned, physical systems, for example halogen lamps or LEDs, are alternatively possible. These may in turn be present (for example, halogen glow lamp or LED inserted in Teflon) in a transparent, scattering or absorbing or luminescing matrix (for example a polymer). Likewise usable are systems that contain physical and chemical components, such as, for example, polymer systems, that contain an LED as an excitation light source and one or more chromophores (emitters, absorbers, scatterers). Luminescence waveguides are also possible here.

According to an additional advantageous embodiment, the optical standard modules comprise at least one scattering module (also called diffuser) for wavelength-dependent or independent diffuse scattering of the entering radiation. The scatter module may be designed as a diffuser plate or as a scattering layer or film of variable thickness. All dye systems (emitters and absorbers and scatterers) may be present inserted in a solid matrix, bound or adsorbed to a solid matrix or as solutions or suspensions (for example colloids), placed in suitable containers of variable layer thickness and form (cells, thin-layer cells, microchannel systems, etc.).

In addition, the optical standard modules may comprise at least one reducer, which reduces radiation intensity (in contrast to absorption standard modules) substantially wavelength-independently, i.e., uniformly over the entire relevant spectral region. In this way, radiation intensity can be adapted to the linearity region of a detector system used or—in the case of highly variably intensively emitting or absorbing modules—their radiation intensities can be adapted to each other. The reducer may with reference to its principal surface running in the x, y plane (that is, orthogonal to the radiation axis z) produce a homogeneous transmission and reduction of radiation or have a transmission and reduction varying gradually or stepwise in the x or y direction. In general, non-fluorescent absorbers, for example gray filters, are used as reducers.

According to another embodiment, the optical standard modules comprise at least one optical filter for stopping out at least one defined wavelength-dependent spectral region. In particular, bandpass filters with variable bandpass in regard to spectral position and breadth (for example notch filters), high-pass or low-pass filters (also called cut-on and cut-off filters) or cut-off filters are possible. In addition, narrow-band absorbers, such as for example holmium oxide, also have a filter function; however, in connection with the present invention these are subsumed under absorption standards. In this connection, (rapidly) saturable absorbers in laser technology, which only open starting from a given amount of entering light, as well as optical switches, for example spiro connections, are likewise known.

According to an additional embodiment of the invention, the optical standard modules comprise at least one mirror module, which partially reflects or substantially totally reflects incident radiation.

In addition, the optical standard modules may comprise at least one mask, which, in at least one x, y direction running along its principal surfaces, has unlike sections that are selected from reflecting or totally absorbing sections, material-free sections (i.e., holes or apertures), scatter sections, mirror sections and reducer sections.

For applications in combination with location-resolving optical measuring methods, such as fluorescence microscopy, a combination with absorbing, emitting (fluorescing) or reflecting structures (structural elements in the nm to cm range) is also advantageous. The optical structural components functioning as masks) (for example, a metal film vaporized onto a quartz, glass or polymer substrate) may serve either for the determination of location resolution in the x, y direction or for example for adaptation to given sample formats such as microtiter plates (well structure) or the modeling of these sample formats.

Additional optical standard modules comprise pin diaphragms of various aperture and polarizers.

With particular advantage, the standard according to the invention may be made available in the form of a kit, which comprises a plurality of separate unlike layer-like optical standard modules joinable to each other plane-parallel, which are suitable for entering into physical interaction with electromagnetic radiation striking one of their two principal surfaces and which in each instance differ from each other by at least one optical property, namely, by their absorption, emission, scattering and/or reflection properties. The standard modules are selected from the group described above, comprising:

(chromophore-based or physical) emission standard modules for the emission of a luminescence spectrum, absorption standard modules for the wavelength-dependent absorption of radiation, scatter modules for the wavelength-dependent or independent diffuse scattering of radiation, reducers for the substantially wavelength-independent reduction of radiation intensity with homogeneous transmission or transmission varying gradually or stepwise along the principal surfaces, optical filter for stopping out at least one defined wavelength-dependent spectral region, mirror modules which partially or substantially totally reflect the radiation, and masks, which in at least one x, y direction running along their principal surfaces, have sections of unlike optical properties, which are selected from reflecting or totally absorbing sections, aperture sections, scatter sections, mirror sections and reducer sections.

An additional aspect of the present invention relates to use of the optical standards according to the invention for the spectral calibration and/or for the characterization of an optical measuring device. The latter may be spectral or integral measuring luminescence-measuring systems, absorption- and reflection-measuring systems (UV/vis/IR), Ulbricht ball-measuring devices (UV/vis/IR; for example, for the measurement of scattering samples), IR and Raman (micro)spectrometers, microscopes (transmission, luminescence, Raman, IR) and optical microtiter plate readout instruments. In particular, any luminescence-measuring and fluorescence-measuring devices, for example fluorescence spectrometers, microfluorometers, microtiter plate readout instruments, confocal imaging systems and scanning imaging systems, such as fluorescence microscopes and laser scanners for microarray technology, can advantageously be calibrated and/or characterized with use of the standard.

Special applications relate to the restorable calibration (i.e., the determination of the (relative) spectral sensitivity), the determination of the wavelength accuracy and of the spectral resolution of the measuring device, as well as use as an intensity standard and as a standard for the determination of the linearity region of the detection system.

The optical sandwich standard according to the invention may exist as a separate structural part that is capable of insertion in standard sample holders, or may be used integrated into other characterizing and calibration tools for optical measuring systems. For example, it is advantageously possible to use a miniaturized sandwich standard or a plurality of miniaturized sandwich standards integrated into a solid matrix (for example, of glass or a polymer) in the form of a slide or a microchannel system as a calibration tool for measuring systems for the readout of microarrays or for microscopes. This also permits combination with additional integrated characterizing and calibrating aids, for example printed, spotted or sputtered chromophores or focusing aids or, in the case of microchannel systems, also structures filled or provided with dyes.

The chromophores may be present singly or in a combination of a plurality of chromophores, unencased or encased, such as, for example, in the form of monochromatically and polychromatically doped particles, dye layers made up of inorganic, organic or inorganic-organic materials, etc.

An additional use of the optical standard according to the invention relates to its use in a barcode system. As in the aforementioned embodiment, in this case, the in particular miniaturized sandwich standard or plurality of sandwich standards is present in a solid matrix, for example of glass or synthetic material, which may be designed as a slide for a microscope or a plate containing a microchannel system and which, for example, has a barcode printed on it.

Additional advantageous embodiments are the subject of the independent claims.

DRAWINGS

Figure 1B:
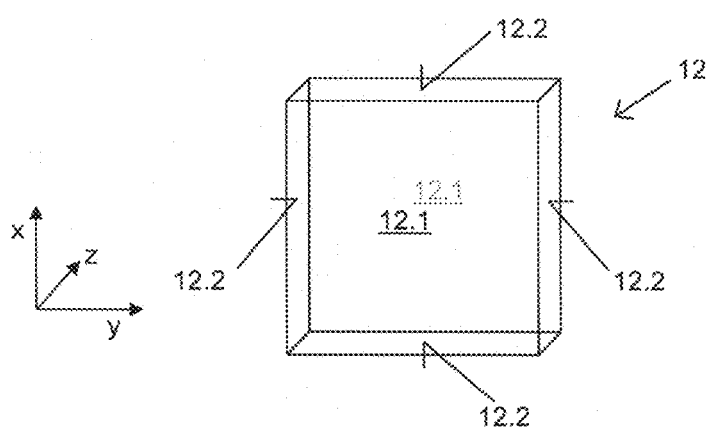
Figure 2A:
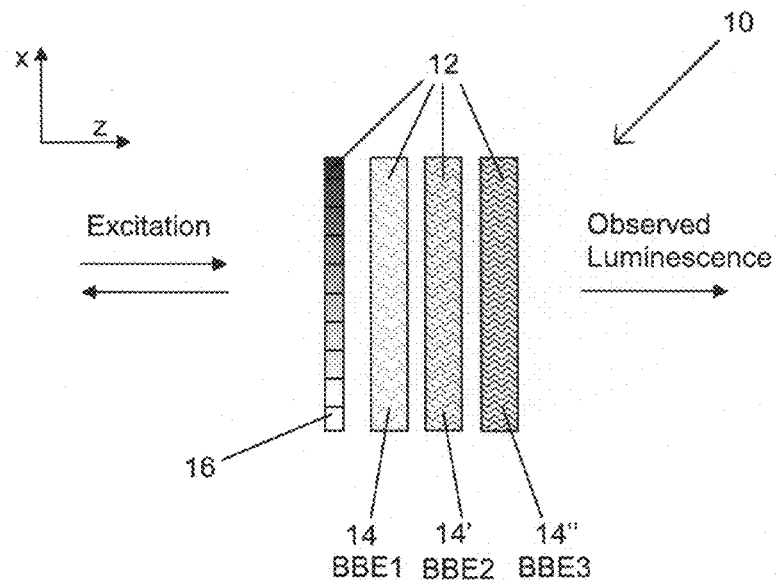
Figure 2B:
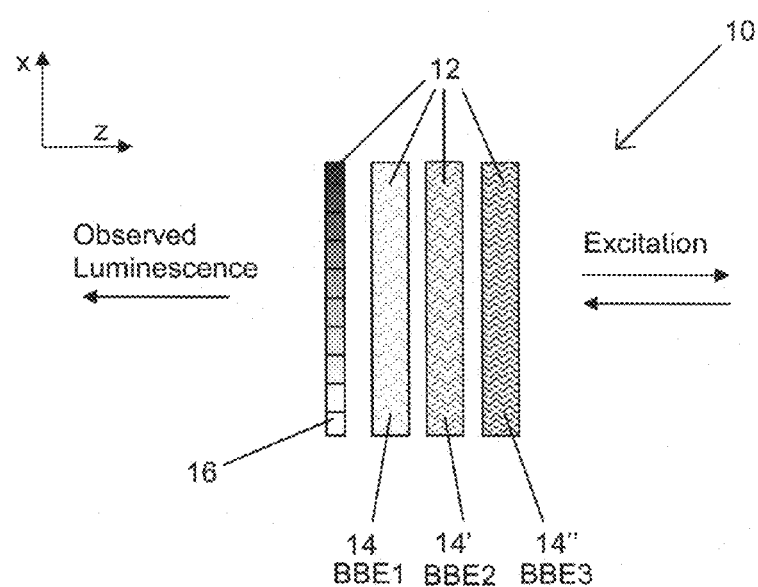
Figure 11:
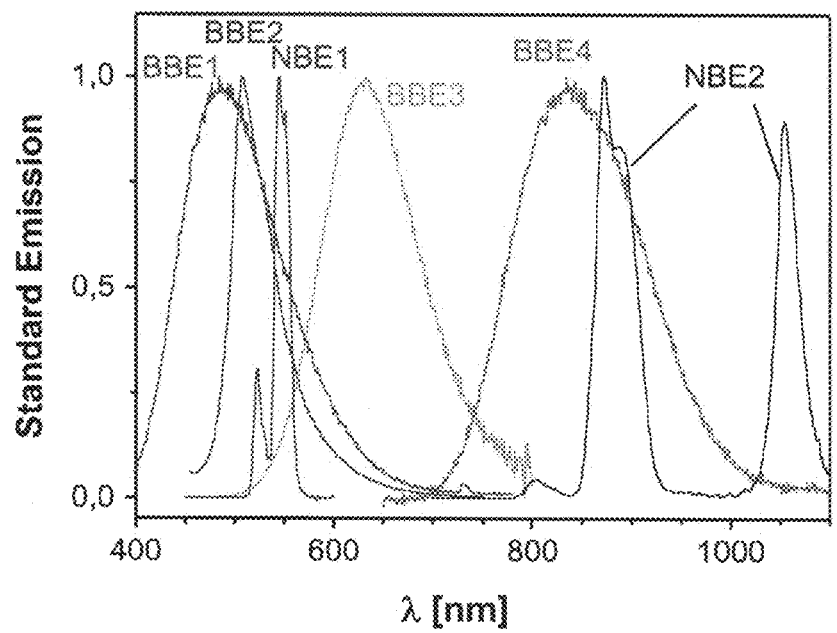
Figure 12:
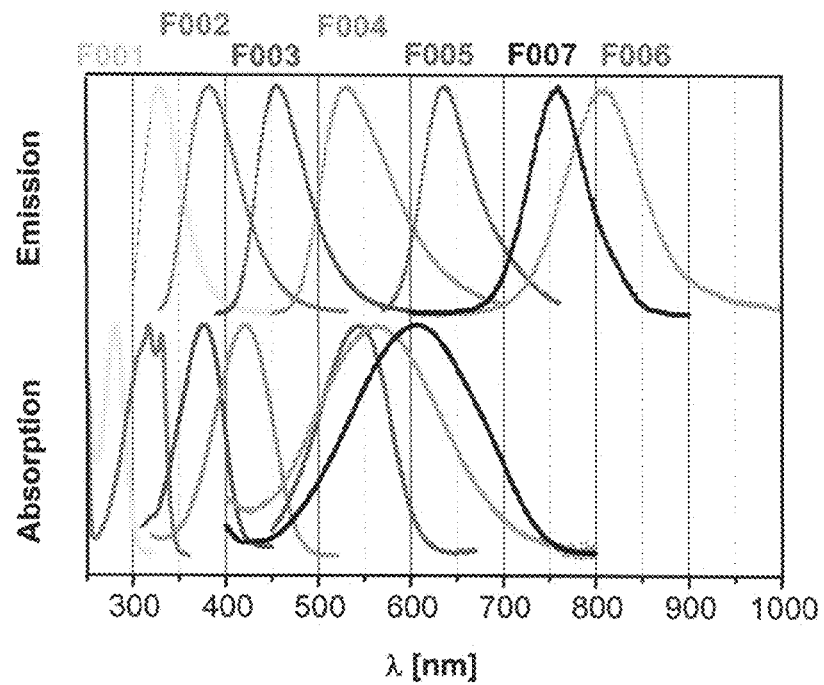
Figure 13:
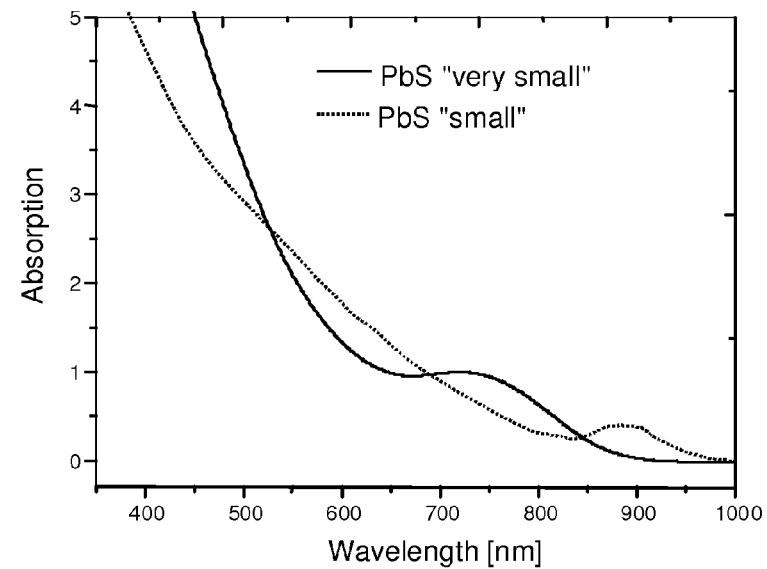
Figure 13:
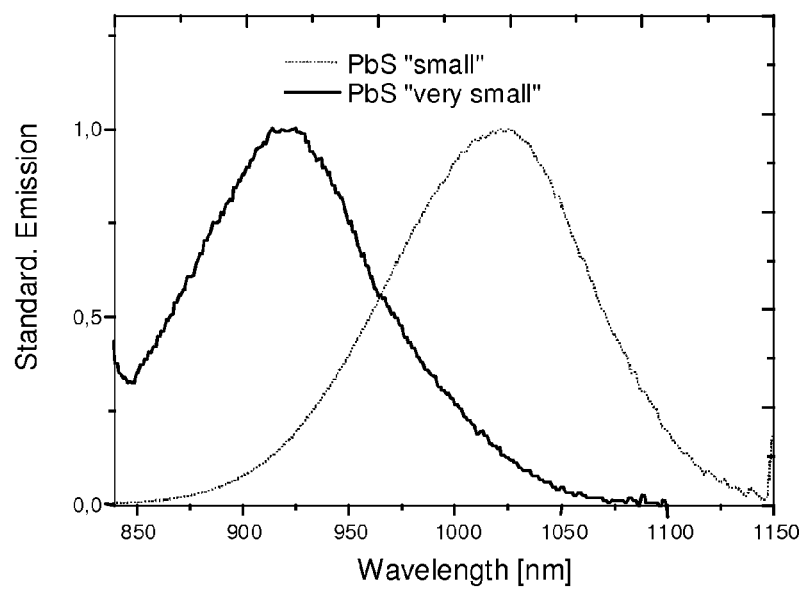
Figure 14:
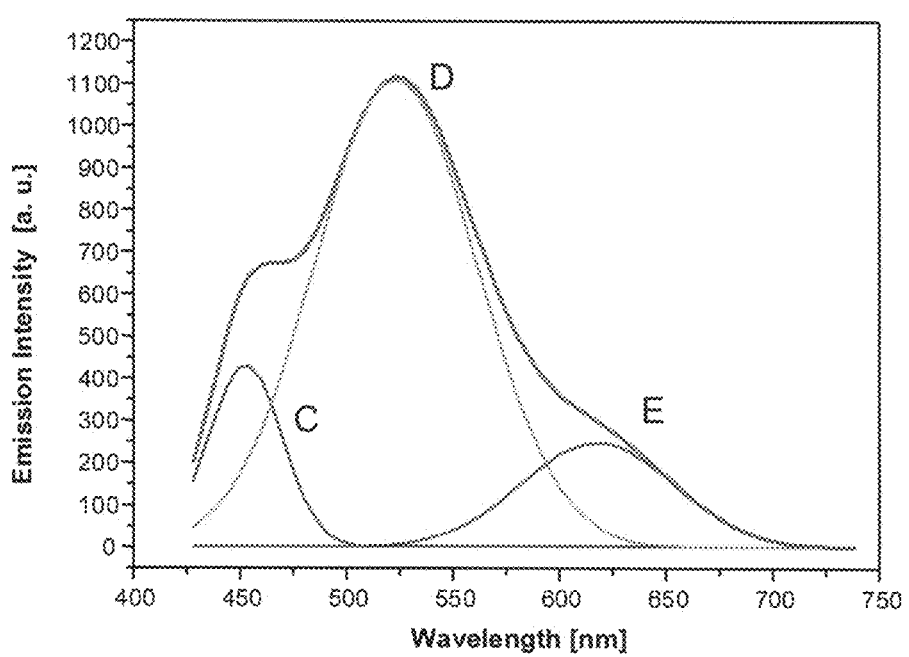
Figure 15:
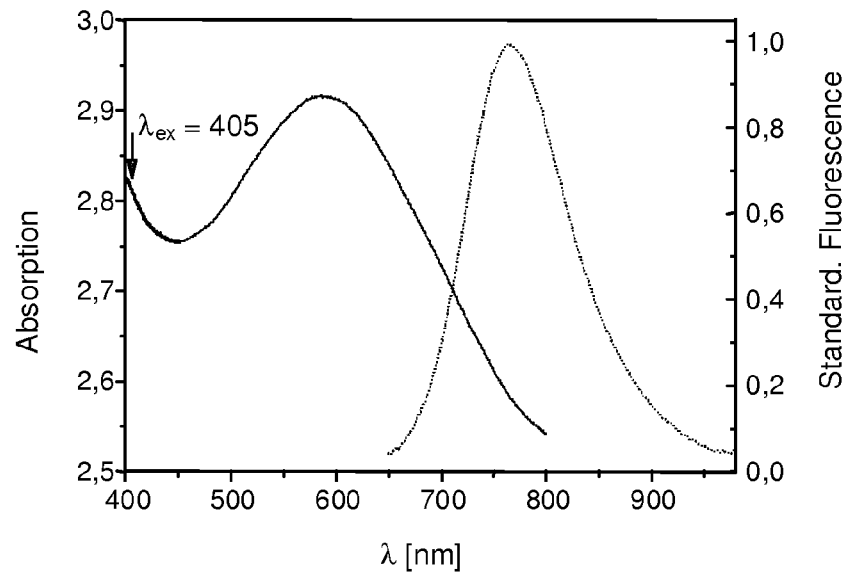
Figure 16:
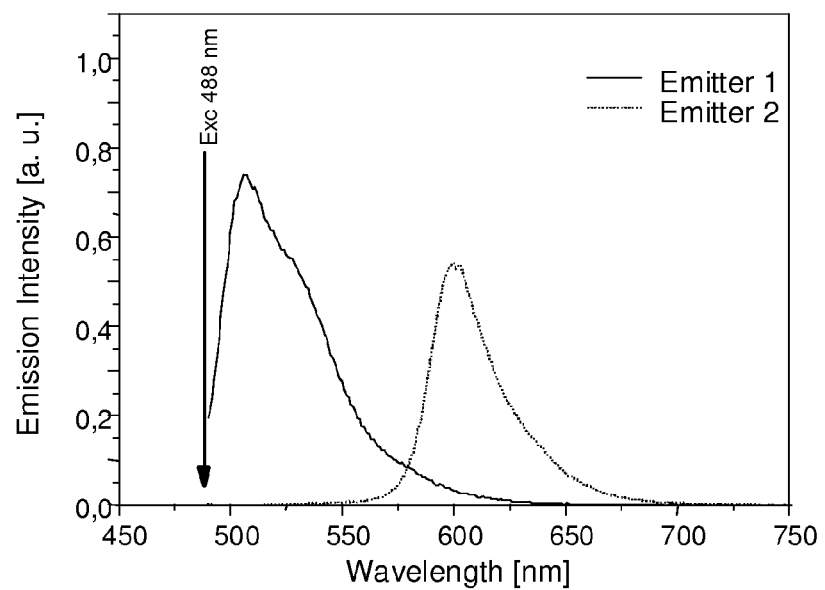

The invention is described in detail below in exemplary embodiments with reference to the accompanying figures, wherein:

FIG. 1A shows a side view of an optical standard according to an advantageous embodiment of the invention;

FIG. 1B, a perspective front view of an optical standard module used in an optical standard according to the invention;

FIGS. 2A and 2B, two possible measuring arrangements of the optical standard of FIG. 1A;

FIGS. 3-10, optical standards according to a variety of advantageous embodiments of the invention;

FIG. 11, emission spectra of typical narrow band-emitting (NBE) and broadband-emitting (BBE) emitters, here of inorganic chromophores in glass matrices;

FIG. 12, absorption and emission spectra of a variety of organic spectral fluorescence standards according to DE 10 2004 044,717 A for the determination of the relative spectral sensitivity of fluorescence-measuring systems and for the determination of the linearity of the detection system;

FIG. 13, absorption spectra (top) and emission spectra (bottom) of PbS nano-crystals of unlike size in toluene, emitting in the NIR spectral region, excited at 405 nm;

FIG. 14, emission spectrum of a combination of three broadband-absorbing and emitting chromophores in ethanol and their individual spectra, excited at 405 nm;

FIG. 15, emission spectrum of a broadband cyanine compound, according to DE 10 2008 040,513.2 in ethanol, absorbing and emitting in the NIR, excited at 405 nm; and FIG. 16, absorption and emission spectra of two typical organic emitters in a polymer matrix, excited at 488 nm.

DETAILED DESCRIPTION

FIG. 1A shows an optical standard 10 according to an advantageous embodiment of the present invention. In this illustration—as in the following—the individual modular components (standard modules 12) of the optical standard 10 according to the invention are shown spaced apart. It is understood, however, that the individual components, which all have a substantially layer-like or disk-like configuration and preferably also corresponding edge lengths with reference to their principal surfaces, are arranged with their principal surfaces directly adjoining each other plane-parallel and joined together. This can be done, for instance, by bonding or welding the surfaces together partially or completely. However, detachable fixing of the optical standard modules 12 together, for example with clips or magnetic holders, is preferable.

According to the invention, the optical standard 10 has a combination of at least two optical standard modules 12, which—depending upon the desired use—each have defined optical properties, in particular a known and characterized absorption, emission or scatter and/or reflection behavior. At the same time, the standard modules 12 in each instance differ from each other by at least one optical property, namely, by their absorption, emission, scatter and/or reflection properties. The standard modules 12 used are made and adapted to each other so that radiation striking one of the two principal surfaces 12.1, which in connection with the present invention are understood as the surfaces running along the x, y plane (see also FIG. 1B), enters into physical interaction with the optical standard module 12 and its material, so as itself to undergo a detectable modulation of its spectral properties and/or its intensity and/or to excite the optical material of the optical standard module 12 to emission of electromagnetic radiation. This physical interaction may take place as wavelength-dependent or independent absorption (optionally with re-emission thereby produced), wavelength-dependent or independent scattering and/or as partial or total reflection.

For clarification of the term "principal surface(s)," FIG. 1B shows a single optical standard module 12 in a perspective view of one of the two principal surfaces 12.1. The two areally greatest surfaces of the layer-like standard modules 12 are designated as principal surfaces, while the four lateral surfaces 12.2 illustrated in FIG. 1B have substantially smaller surfaces. In addition, by "layer-like or disk-like" is meant an outer form that comprises two principal areally dominating surfaces 12.1 arranged plane-parallel to each other, while an outer contour may be designed in any way, for instance square, as here, or round. In the built-in state of the standard module 12, radiation emitted by a light source of the measuring device along the z axis strikes one of the two principal surfaces substantially orthogonally, so as to enter into the already mentioned interaction with the material of the standard module 12.

Since interaction of the radiation with all optical standard modules 12 used is desired, the latter are made, arranged and adapted to each other so that they are at least partially permeable to the radiation applied, so that the hindmost optical standard 12 in the path of radiation is also reached by the radiation.

In general, the optical standard modules 12 may be an absorption standard module or a combination of a plurality of absorption standard modules, which are characterized by a defined (known) wavelength-dependent absorption spectrum, where depending upon the type of the measuring device to be characterized or calibrated, the absorption bands of an absorption standard module may lie in the UV, vis, NIR or IR spectral region, so that they can be used in UV, UV/vis, (FT)IR or Raman spectrometers as well as luminescence-measuring systems.

In addition, the optical standard modules 12 may be an emission standard module or a combination of a plurality of emission standard modules, which have or consist of a material that, after excitation by suitable radiation, is converted into an excited state and upon return into the basic state again releases the absorbed energy as photoluminescence, i.e., as phosphorescence or fluorescence. Thus, the emission standard modules in each instance have a defined emission spectrum, the emission bands of which, as in the case of the absorption standard modules, may lie in the UV, vis, NIR or IR spectral region and in this way may find use in luminescence-measuring devices, in particular fluorescence-measuring devices.

Additional standard modules 12 may be used and in particular be combined with emission and/or absorption standard modules, for example scatterers (also called diffusers), reducers, filters, partially permeable or impermeable mirrors and masks, which have a variety of the aforementioned elements in sectionwise distribution in the x, y plane. These will be explained in greater detail below. However, it is preferably provided that at least one emission standard and/or one absorption standard module be used in the optical standard 10 according to the invention.

In the example shown in FIG. 1A, the optical standard 10, usable as a spectral fluorescence standard, comprises a total of three emission standard modules 14, 14' and 14" combined with each other, which here in particular are designed as broadband-emitting standards BBE1, BBE2 and BBE3. Here, the chromophores, realized as chromophore-based (chemical) broadband emitters in this example, preferably are selected so that their combined emissions cover as great as possible parts of the UV/vis/NIR spectral region and ideally can be excited at a single excitation wavelength. Examples of emission spectra of inorganic chromophores present in glass matrices, which are usable for this application, are shown in FIG. 11 (see there the broadband emitters BBE1, BBE2, etc.), while FIG. 12, upper part (see there, for example, the emitters F003, F004, F005) and FIG. 14 show the emission spectra of suitable organic chromophores in solution. It is likewise possible to use—optionally in combination with the aforementioned—nanocrystalline substances, such as PbS in polystyrene, the spectral position of which can be adjusted within a broad NIR region by the particle size (FIG. 13, bottom). Should the spectral region of the emission be extended into the NIR region, the NIR dye shown in FIG. 15 may in particular alternatively be combined with other chromophores or standards.

The optical standard 10 according to the invention shown is in particular used in order to perform a spectral calibration of the measuring system used. For this, an emission spectrum of the standard 10 is measured with the measuring system to be calibrated, which has the standard-specific as well as the instrument-specific spectral constituents, and the measured spectrum is divided by the known standard spectrum. The correction function so obtained contains all instrument-imposed spectral constituents. If an emission spectrum of an unknown sample is subsequently absorbed by the measuring system, this spectrum need only be multiplied by the correction spectrum in order to calculate the instrument-imposed spectral constituents.

The standard 10 shown in FIG. 1A additionally comprises, in addition to the for example three emission standard modules 14, 14', 14", a reducer 16, which undertakes an adaptation of the fluorescence intensity in the linear measuring region of the fluorescence-measuring system to be characterized. In particular, a multifunctional reducer, variable in the x direction (or the y direction), which consists of a plurality of reducers arranged adjacent in the x, y plane, of graduated transmission along the x axis, may be used. Alternatively, such a variable reducer may be realized by, for example, a strip-like reducer, which may be arranged displaceable at selected positions along the x, y plane. The use of a (variable) reducer 16 allows the standard 10 to determine—in addition to the spectral correction explained above—the linearity region of the detection system over a very broad spectral region. Similarly, in this way, the intensity of the standard and the intensities of individual standard modules can be adjusted in defined fashion.

Alternatively, instead of the reducer 16, for example a bandpass filter with spectral position of the bandpass variable in the x direction (or the y direction) may be used in order thus to produce structures in the resulting mixed spectrum of the emitter. The combination of emitting dyes with bandpass or cut-off filters permits spectra with variable shape in a variety of spectral regions to be produced from any structured or broadband emission spectra (spectral shaping). Hence, spectrally adapted or wavelength-selective intensity control is also possible. If a known standard (fluorescence) is used in a complex layer system, its spectral characteristic is influenced when an absorption spectrum of one layer overlaps a luminescence spectrum of another layer. The possibility of selective "spectral shaping" is thus automatically provided. Should the influence of absorption need to be minimized, thin layers must be used.

A particular advantage of the optical standard 10 according to the invention is its suitability for being used in two directions, i.e., for being irradiated and/or observed in the +z or the −z direction. This is illustrated in FIGS. 2A and 2B for the optical standard 10 of FIG. 1A. In FIG. 2A, irradiation takes place in the −z and +z directions, and the observation of luminescence (taking place in all directions) takes place in the −z direction. According to the direction of excitation selected, this is the transmission and re-emission direction. On the other side, in FIG. 2B, irradiation takes place in the −z and +z directions, while the observation of luminescence takes place in the +z direction. According to the definition used here, observation is always made against the direction of diffusion of luminescence. This variable measuring arrangement permits use in a variety of measurement geometries, in order so to supply a variety of intensities or intensity ratios for controllably adjustable spectral regions and spectral patterns.

Figure 3:
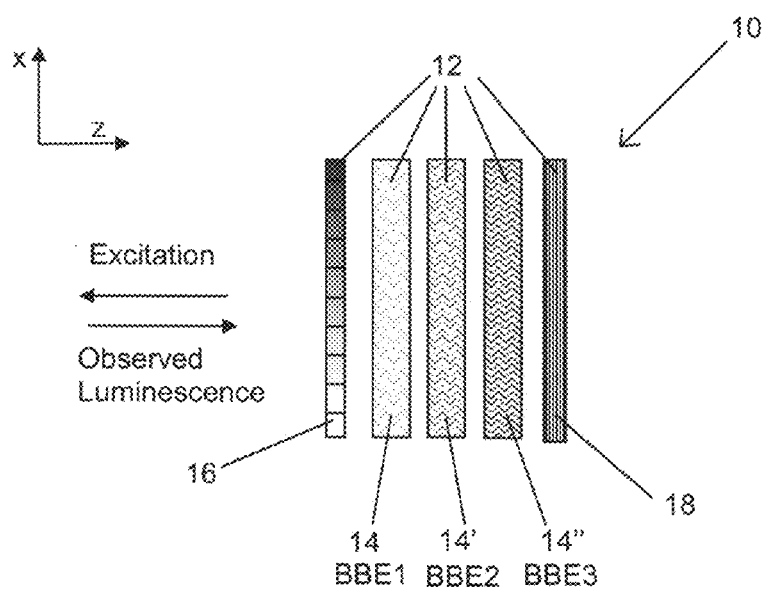

A modification of the standard 10 shown in FIGS. 1 and 2 is illustrated in FIG. 3. Here, the standard 10 has, in addition to the combination of broadband emitters (emission standards 14, 14', 14") and the reducer 16, a (substantially totally reflecting) mirror 18. In this way, the same emission standard combination can also be used in measurement geometries in which excitation takes place in the +z direction, and detection of the reflected and re-emitted luminescence radiation takes place in the −z direction (so-called 0°/360° geometry). Due to the total reflection of luminescence and of the exciting radiation at the mirror 18, the observed intensities are enhanced.

Figure 4:
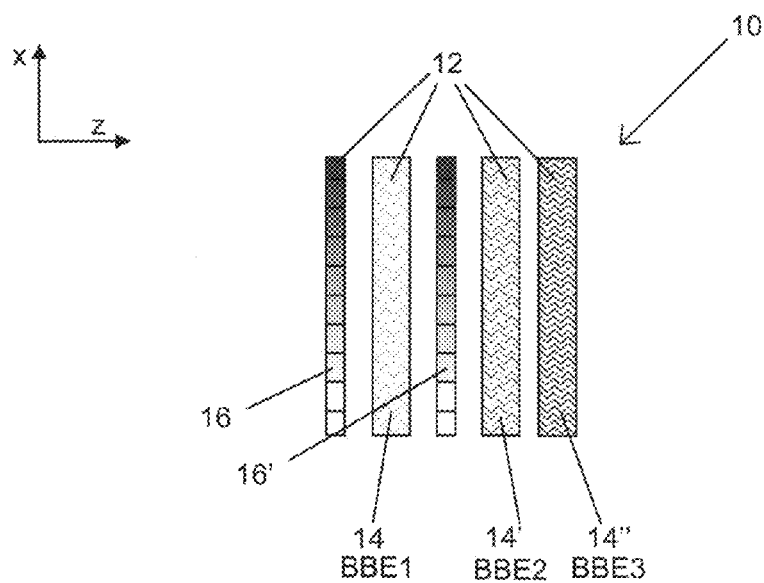

An additional modification of an optical standard 10, usable as a spectral fluorescence standard and/or as an intensity standard, with three emission standards 14, 14', 14", which in turn are designed as broadband-emitting chromophores BBE1, BBE2 and BBE3, is shown in FIG. 4. The standard 10, like the one shown in FIG. 1A, has a first reducer 16 preceding it in the direction of radiation. In addition, a second reducer 16' is provided between the first emission standard 14 and the second emission standard 14'. In this way, for example at very variously strongly emitting standards, the intensities of the various emitters can be adapted to each other or defined intensity ratios of the emitters can be adjusted, in order finally to obtain constant intensity ratios of various emitters. Should the spectral profiles of the emissions of the emitters be adapted, instead of or in addition to the reducers 16, 16', bandpass filters may alternatively be used, the transmission of which has very strong wavelength dependence in a narrow spectral region. The various measuring arrangements and variants according to FIGS. 2A, 2B and 3 are also realizable in the embodiment shown in FIG. 4.

Figure 5:
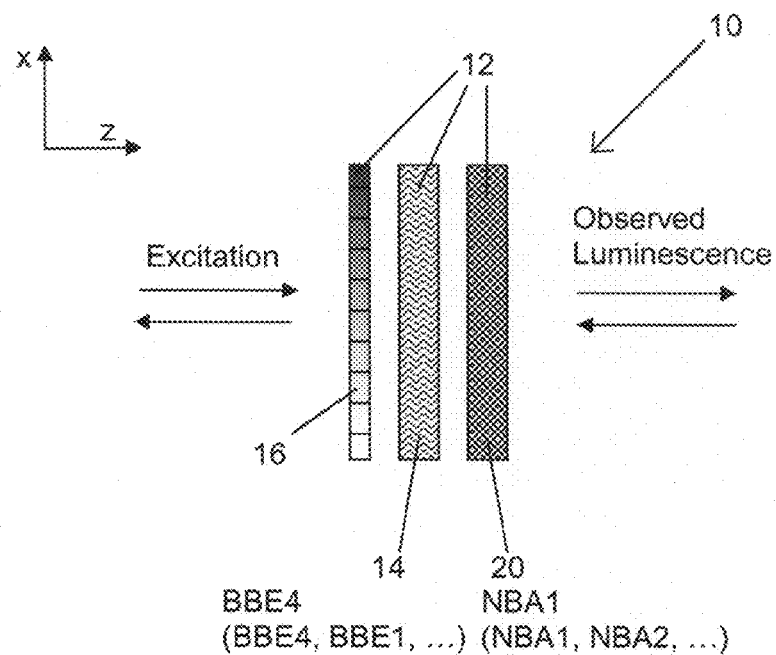

Another principle of an optical standard 10 according to the present invention, which may be used as a spectral fluorescence standard and/or as an intensity standard, is illustrated in FIG. 5. Here, a broadband-emitting emission standard module 14 (BBE4) is combined with a narrow band-absorbing absorption standard module 20 (NBA1), for example in the form of a holmium oxide glass. There, the two modules are selected so that at least one narrow absorption band of the narrow band-absorbing chromophore of the absorption standard module 20 spectrally overlaps with at least one broad band of the emission standard module 14. The resulting total spectrum of the standard 10 thus has at least one broad band with at least one relatively sharp absorption line. In this way, any structured spectra can be produced by skillful utilization and combination of the emissions from suitable emission standards and of absorption of the emitted radiation by suitable absorption standards. Alternatively, (as in FIG. 1A), a combination of a plurality of broadband emitters (BBE1, BBE2, etc.) or alternatively, a physical standard, for example a halogen lamp, may be used as a broadband emission standard 14. Likewise, a plurality of narrow-band absorbers with many different absorption lines may be combined to make a fluorescence standard with an emission spectrum with line-like bands, structured over a broad spectral region, the intensity of which can be controlled by one or more reducers 16 (optionally with variable reduction along the x axis). If instead of the reducer combination 16, bandpass filters are used, the intensity ratio of the individual bands to each other can in addition be regulated and adjusted in defined fashion.

The arrangement illustrated in FIG. 5 may be used in a transmission and re-emission arrangement. In order to observe the luminescence spreading out in the +z direction as unstructured spectrum in the −z direction, excitation is effected in the +z direction. In this arrangement, re-emission (luminescence spreading in the −z direction) can likewise be detected in the +z observation direction. If excitation is effected in the −z direction, a structured luminescence spectrum, reduced by the filter, can be detected in the +z observation direction and, correspondingly, in the re-emission arrangement (−z observation direction), a non-structured luminescence spectrum, which has undergone no reduction by filters, can be picked up. (The luminescence radiation is always observed against its direction of spread.) The combination may find use, for instance, as a standard (spectral standard, intensity standard and quantum yield standard) for the characterization of Ulbricht ball systems.

Figure 6:
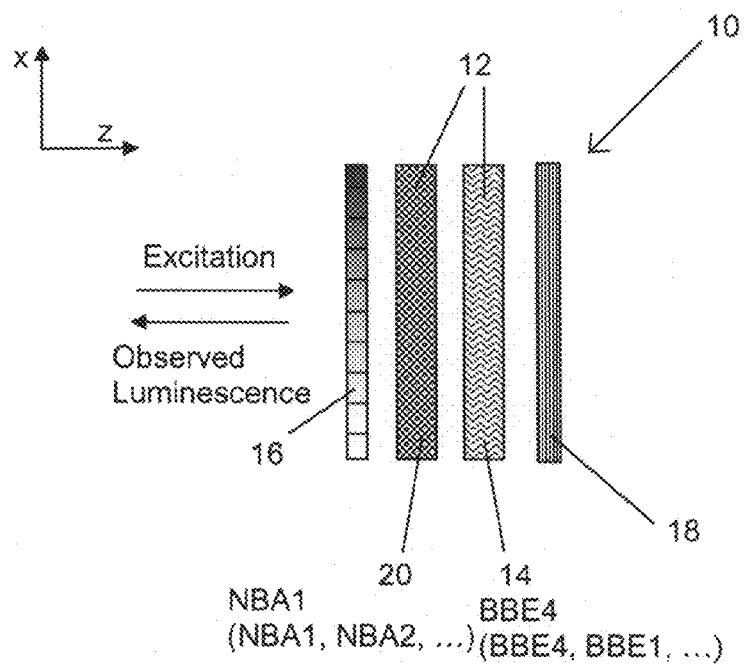

FIG. 6 shows a modification of the standard of FIG. 5. In this case, the standard 10 comprises (in this sequence) an (optionally graduated) reducer 16, one or more narrow band-absorbing absorption standard modules 20, one or more broadband-emitting emission standard modules 14 and, as a last module 20 in the path of radiation, a mirror 18, so that observation takes place in the +z direction (spread of luminescence in the −z direction). This arrangement may find use, for example, in microscopes or microtiter plate readout instruments or in other confocal and scanning imaging systems.

Figure 7:
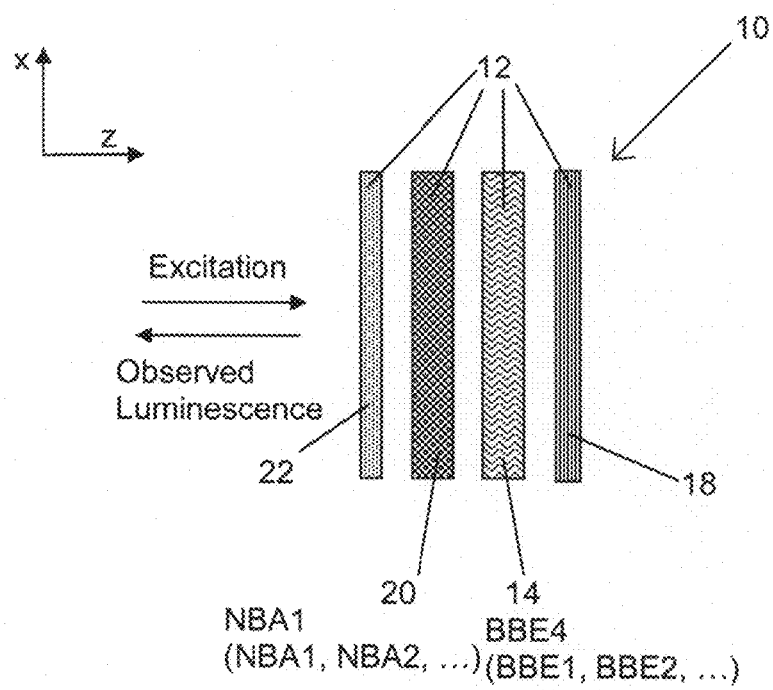

Another modification of the standard in FIG. 6 can be seen in FIG. 7, where instead of the reducer 16, a scatter module (diffuser) 22 is arranged, which ensures homogeneous illumination of the standard 10 and sample space. Accordingly, in addition to inhomogeneities of illumination, anisotropy effects of the standard can also be distinctly reduced. In addition, effects of the excitation radiation geometry are reduced, i.e., the standard becomes insensitive with respect to the excitation geometry (for example, upon excitation with focused light). Alternatively, a plurality of diffusers 22 and/or combinations of diffusers and reducers 16 may be arranged at various locations along the z axis. Diffusers may advantageously also be used in combinations with the other optical standards 10 shown in FIGS. 1-6 and 8-12.

Figure 8:
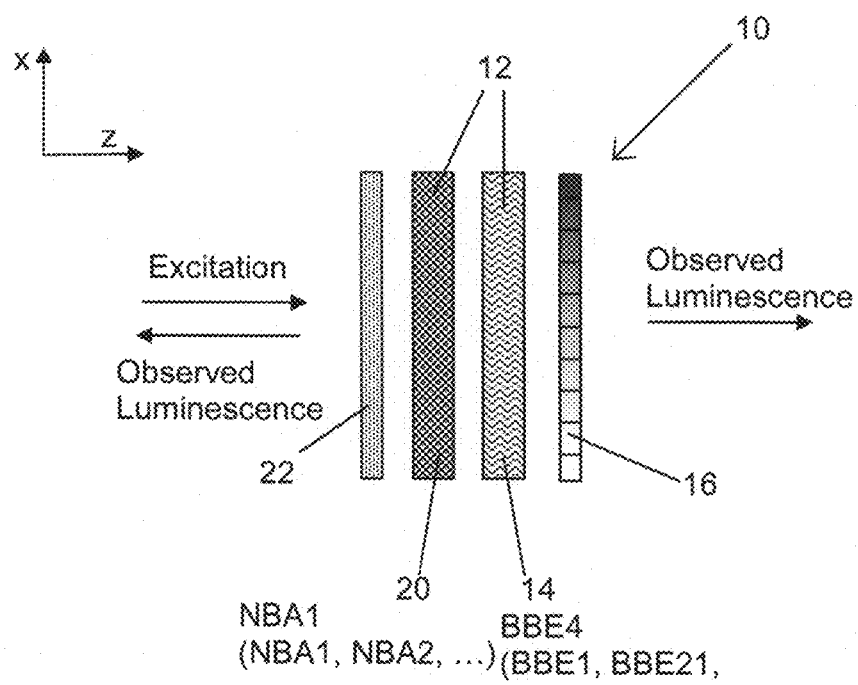

The optical standard 10 of FIG. 8 shows a development of the standard 10 of FIG. 5, which, in addition to the latter, has a scatter module (diffuser) 22 for the homogenization of illumination. The luminescence can be observed from both directions. As in FIG. 7, the diffuser 22 may also be positioned differently, for instance between the modules 14 and 20. And, instead of the absorption standard module 20, one or more additional emission standard modules 14, or various reducers 16 at various positions similar to FIG. 4, may be used.

Figure 9:
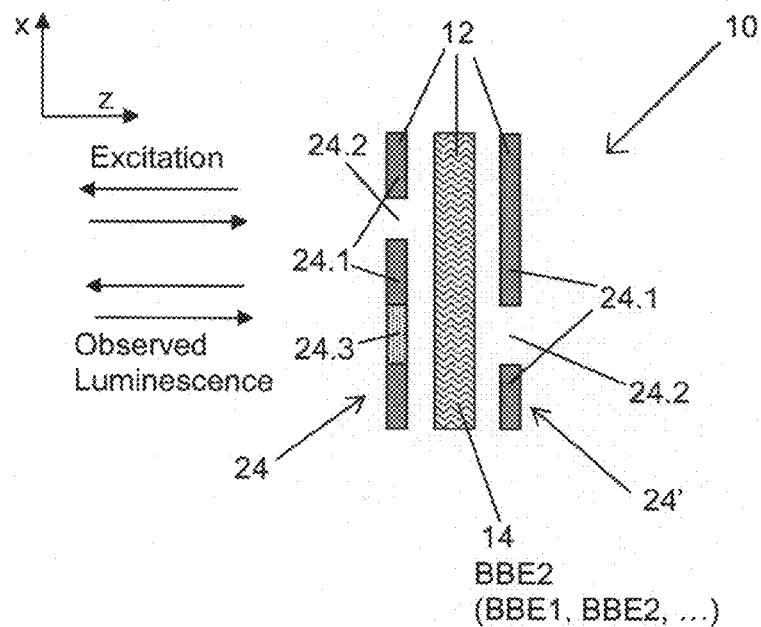

In FIG. 9, an emission standard 14, in particular a broadband-emitting emitter BBE2 or a combination of a plurality of such emitters, is arranged between two masks 24 and 24', which along the x-y plane have unlike sections with unlike optical properties and functions. In particular, the masks 24, 24' have sections 24.1 with one-sided or two-sided (i.e., on one or on both principal surfaces 12.1) reflecting or absorbing materials or coatings with such, which limit material-free sections 24.2, in other words, apertures. Thus, at locations on the x, y plane with reflecting or absorbing sections 24.1, the mask is practically completely impermeable to radiation and the material-free sections 24.2 are practically completely permeable to radiation. Reflecting coatings may be realized, for example by silver layers, while absorbing layers, which, in contrast to the absorption standard modules 20, absorb practically completely in the entire wavelength region of interest, can be realized for example by black carbon layers or carbon incorporated in a variety of matrices, carbon nanotubes, "black" non-fluorescing dyes (for example, NPL Black) or dye layers or eloxation. In addition, the masks 24 may have sections that are designed as diffusers, reducers or mirrors of variably strong transmission. A section 24.3, designed as a diffuser, of the mask 24 is illustrated in FIG. 9 by way of example.

Figure 10:
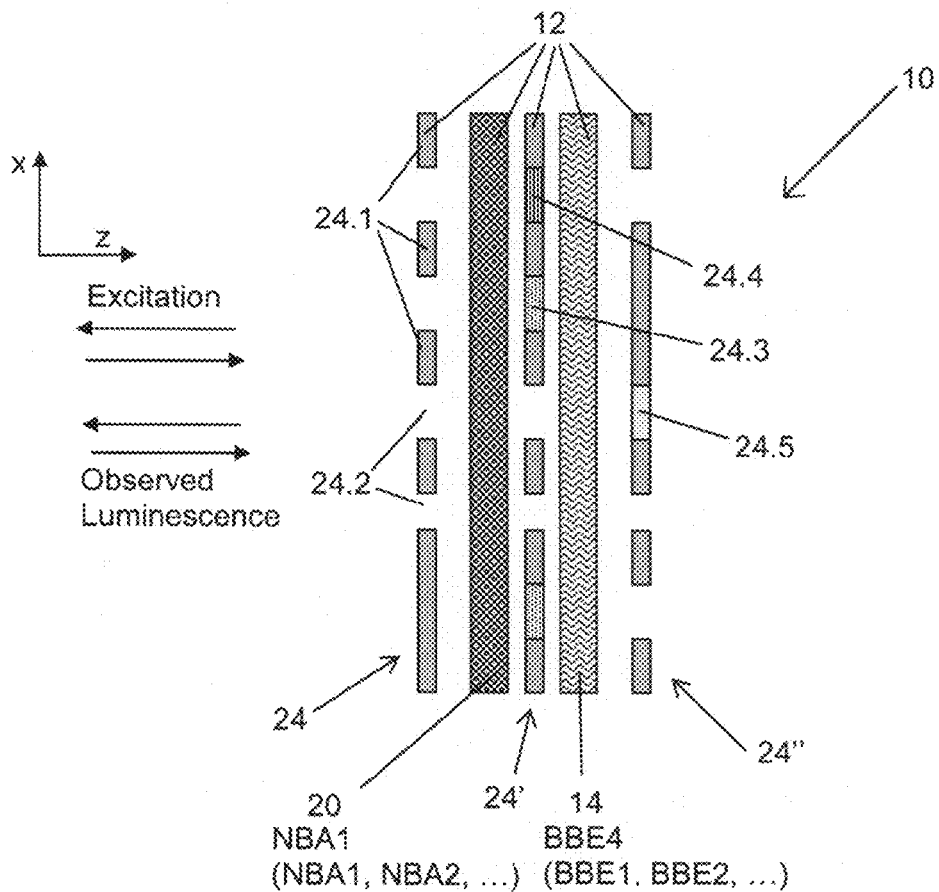

The optical standard of FIG. 10 has, in addition to a combination of at least one narrow band-absorbing absorption standard 20 (NBA1) and at least one broadband-emitting emission standard 14 (BBE4), three masks 24, 24' and 24", which, in addition to the reflecting and (totally) absorbing sections 24.1, have material-free sections 24.2 (apertures) as well as diffuser sections 24.3, mirror sections 24.4 and reducer sections 24.5. Instead of the absorption standard module 20, an emission standard module or a combination of a plurality of emission standard modules may be provided.

The standards of FIGS. 9 and 10 may be used in transmission and reflection. The masks may also be used in combination with the standards described above.

The embodiments of the optical standard 10 according to the present invention, described above only by way of example, illustrate its manifold possible uses and variations. They can be used multiply in two directions, i.e., irradiated and/or observed in the +z as well as in the −z direction, where some properties of the standard can be adjusted direction-dependently. Suitable selection of emission and/or absorption standard modules, optionally combined with additional modular components, such as reducers, diffusers, mirrors and/or masks, allows virtually any modulated total spectra, in particular emission spectra, to be produced.

Some examples of emission spectra of a great variety of chromophores which may advantageously find use in emission standard modules 14 and in some cases also in absorption standard modules 20, are illustrated in the following FIGS. 11 to 16, some of which have already been mentioned in connection with the standards 10, discussed above.

Thus, FIG. 11 shows emission spectra of typical inorganic narrow-band emitters (NBE1 and NBE2) and broadband emitters (BBE1 . . . 4), which are present in glass matrices. In contrast, the absorption and emission spectra of various broadband-emitting organic spectral emission standards (fluorescence standards) in solution (ethanol in the case of F001-F005 and F007 and acetonitrile for F006), which are disclosed in DE 10 2004 044,717 A and the use of which in connection with the present invention is expressly included, are shown in FIG. 12. Because of the smooth and broad band courses of their emission and absorption spectra, as well as their coverage of a broad spectral region, these dyes are suitable for determination of the relative spectral sensitivity of fluorescence-measuring systems and, specifically, also for the emission as well as for the excitation correction and for determination of linearity of the detection system. If combinations of these fluorophores are used as emission or absorption standards in an optical standard according to the present invention, the spectral sensitivity of the measuring system can be determined over the entire spectral breadth shown with only one single measurement or a small number of measurements. In addition, almost any structured or modulated spectra can be produced, for example, by combination with narrow-band emitters or absorbers or filters (spectral shaping), which can be used for multiple characterization applications, for example for application as a standard for the testing of wavelength accuracy and spectral resolution or as a day-to-day intensity standard or spectrally adapted intensity standard.

FIG. 13 shows absorption spectra (top) and emission spectra (bottom) of commercially available PbS nanocrystals of nanometer sizes emitting in the NIR spectral region in two unlike sizes ("very small" and "small"), excited at 405 nm. The nanocrystals preferably are present in colloidal "solution," here in toluene, in which the sterically or electrostatically stabilized solid particles do not precipitate. In principle, PbS nanocrystals with emissions in the spectral region of about 850 nm to 1750 nm can be produced, where the spectral position of the first excitonic absorption maximum and the spectral position of the emission maximum can be controlled by the particle size. Similar absorption and emission spectra are obtained, for example, in solid matrices, for example PMMA or polystyrene. Excitation of the emission is in principle possible at all wavelengths at which the nanocrystals absorb.

FIG. 14 shows a combined emission spectrum of a dye mixture (mixing ratio of parent solutions: 1:1:1) in ethanol with minimal dye-dye interaction, consisting of three broadband-absorbing and emitting chromophores (C, D, E), excited at 405 nm, as well as the respective individual spectra at like excitation wavelength. Very similar absorption and emission spectra result for example for a combination of containers or layers of the dyes C, D and E individually dissolved or embedded in a solid matrix. An intensity adaptation can be obtained—even without change of concentration—by incorporation of a reducer selectively arranged in the direction of radiation before the dye D (and behind C and E). Advantageous in the combination indicated is the excitability of all three chromophores at the same wavelength, namely, at 405 nm, which is a common excitation wavelength of many luminescence-measuring systems.

The broadband-absorbing and emitting NIR chromophore on which the emission spectra shown in FIG. 15 is the subject of the later application DE 10 2008 040,513.2, the use of which in connection with the present invention is expressly included. The left band shows the emission in a polar solvent (ethanol), while on the right, the emission band of the dye is shown in a comparable non-polar solid matrix (polystyrene), excited at 405 nm in each instance. The broad unstructured emission spectrum exhibited by this chromophore in polystyrene is a prerequisite for use as a spectral emission standard for the determination of the relative spectral sensitivity of luminescence-measuring systems, made possible in elegant fashion but also by spectral shaping, for example, with narrow-band absorbers. This dye may be combined with, for example, the chromophores shown in FIGS. 11 to 14 to make a "sandwich standard" 10 according to the invention, per FIGS. 2 to 4, which collectively can be excited to emission at the common diode laser wavelength of 405 nm.

The absorption and emission spectra of two typical organic emitters, here incorporated in a polymer matrix, which are combined to make a sandwich standard, can jointly be excited at 488 nm, illustrated in FIG. 16.

The invention involves a variable approach for standards and reference materials with problem-adapted adjustable absorption, luminescence, scatter and reflection properties in the UV/vis/NIR spectral region for the restorable calibration and characterization of optical measuring systems, in particular spectrally and integrally luminescence-measuring systems. The sandwich standards according to the invention, usable in any measurement geometries on both sides (in the +z direction and in the −z direction), are in addition in principle also suitable for the characterization of all measuring instruments that measure transmission, absorption and/or scatter. These standards may be used as separate calibrating tools as well as incorporated into instruments to be characterized. Here, application-specifically controllable are in particular the spectral region, the emission, the emission intensities, the spectral position and the band shape of the emission. The standards are designed so that their optical properties can in addition be varied and controlled by the measurement geometry used. The spectral region-, intensity- and measurement geometry-adaptable application-specific selection and combination of various absorbing, emitting and scattering or reflecting components form the novel basis for this approach.

There, the novelty of these sandwich standards consists in that from a limited number of novel or known materials, well characterized with reference to their optical properties, novel standards with problem-adapted absorption, emission and scatter properties can be produced again and again by skillful and problem-specific combination at comparatively little expense. Hence, a platform of standards for a great many different applications of various optical measuring techniques, such as luminescence techniques, and the determination and control of many different instrument and material parameters is procured. These sandwich standards are in principle usable in two different measuring arrangements, the standards being designed so that their optical properties can be varied and controlled by the measurement geometry used. Thus, the sandwich standards are suitable for the characterization of luminescence-measuring systems as well as for the characterization of all measuring instruments that measure transmission, absorption and/or scatter.

The various components of these sandwich standards are placed one after another defined in the z direction, for example by bonding, welding or preferably by the use of holders such as clips or magnetic holders, for example for applications in connection with fluorometers, microfluorometers and fluorescence sensors (use in front-face geometry). For applications and luminescence methods, in which measurements are made on planar or structured "horizontal" systems and samples, such as, for example, a microarray or a microscope slide or a microtiter plate, these sandwich standards are positioned perpendicular to the exciting light. For possible applications in a 0°/90° measurement geometry, the components of the sandwich standard are adapted to the desired application on the excitation and emission side. For example, spectra with variable shape in a variable spectral region can be produced by the combination of dyes with bandpass or cut-off filters in any x broadband or structured emission spectra (spectral shaping), which are suitable for and can be adapted to a great many different calibration and characterization problems and can be adapted for use as reference systems for signal intensities.

Depending upon the components used, the sandwich standard can be used for the determination of wavelength accuracy and the spectral resolution of luminescence-measuring systems (for example, a combination of a variety of narrow band-emitting fluorophores or a combination of one or more broadband emitters with one or more narrow-band absorbers). Use as an intensity standard with precisely adjustable emission intensity and precisely adjustable spectral properties (for example, a combination of a broadband emitter with a narrow bandpass filter for adaptation of the emission profile and combined with a reducer for the adaptation of emission intensity) is especially attractive. An additional application is determination of the linearity region of detection systems (either various sandwich standards, which differ, for example, with reference to transmission of the reducers used, or use of a reducer with varying transmission in the x direction). Application as an intensity standard can then also include use as an internal (integrated into the measuring system to be characterized) or external (not integrated into the measuring system to be characterized) standard for the referencing of measuring signals and as a constant reference system for fluorescence intensities. This also applies mutatis mutandis to the function as a spectral standard. The combination of various broadband-emitting chromophores (chromophores with or without minimal integration or energy-transfer cascade and cascade systems; nanocrystal systems with particle size-controllable spectral position of absorption and emission and the represented NIR chromophore), ideally excitable at one wavelength, which are found either individually or in a plurality in a variety of solid matrices or in a variety of liquid matrices (in suitable containers), can be used for determination of the (relative) spectral sensitivity of fluorescence-measuring systems (emission correction) over a very broad spectral region. This is very attractive in regard to the fact that simple chromophore systems and spectral fluorescence standards and/or emission standards in a single measurement cover only one spectral region of at most 150-200 nm (vis region; example, quinine sulfate). This also applies to combinations and sets of spectral standards that typically all must be excited at different excitation wavelengths for emission. Additional options are the combination of fluorescing and scattering systems for determination of the homogeneity of illumination in imaging methods and the combination of fluorescing systems with structured applied absorbing or reflecting materials functioning as masks.

In addition, the sandwich standards are suitable for the characterization of spectrometers that work in 0°/180° measurement geometry (transmission and absorption, calibration with/without fluorescence) and for the characterization of Ulbricht ball-measuring systems (standards with defined optical properties with/without luminescence), as well as for IR and Raman spectrometers.

What is claimed is:

1. An optical standard for the calibration or characterization of optical measuring devices or as intensity-reference system for intensity measurements, comprising a combination of at least two layer-like optical standard modules having defined optical properties, joinable or joined together substantially plane-parallel, wherein the standard modules in each instance differ from each other by at least one optical property, namely, by at least one of their absorption properties, emission properties, scatter properties and reflection properties, and the standard modules are made so that they enter into physical interaction with electromagnetic radiation striking one of their two principal surfaces, wherein the optical standard modules comprise at least one emission standard module for the emission of a luminescence spectrum and wherein the optical standard modules comprise a combination of a plurality of emission standard modules, which are adapted to each other so that their emission bands partially overlap each other.

2. The optical standard according to claim 1, wherein the optical standard modules comprise at least one absorption standard module for the wavelength-dependent absorption of the electromagnetic radiation.

3. The optical standard of claim 2, comprising a combination of a plurality of absorption standard modules, which are adapted to each other so that their absorption bands partially overlap each other.

4. The optical standard according to claim 1, wherein the optical standard modules comprise at least one scatter module for the wavelength-dependent or wavelength-independent diffuse scattering of the electromagnetic radiation.

5. The optical standard according to claim 1, wherein the optical standard modules comprise at least one reducer module for substantially wavelength-independently reducing an intensity of the electromagnetic radiation, either homogeneously or with transmission varying gradually or stepwise along its principal surfaces.

6. The optical standard according to claim 1, wherein the optical standard modules comprise at least one optical filter for stopping out at least one defined wavelength-dependent spectral region.

7. The optical standard of claim 6, comprising at least one of a bandpass filter and a cut-off filter.

8. The optical standard according to claim 1, wherein the optical standard modules comprise at least one mirror module for partially or substantially totally reflecting the radiation.

9. The optical standard according to claim 1, wherein the optical standard modules comprise at least one mask comprising sections of unlike optical properties, wherein the sections are arranged at least on one x, y direction running along the module's principal surfaces and are selected from reflecting sections, totally absorbing sections, aperture sections, scatter sections, mirror sections and reducer sections.

10. The optical standard according to claim 1, comprising a combination of at least two broadband-emitting emission standard modules for the emission of at least one broad luminescence band, the emission bands of which are spectrally adapted to each other to partially overlap each other, and further comprising at least one of a reducer module and of a diffuser module.

11. The optical standard of claim 10, further comprising a mirror module for partially or substantially totally reflecting the radiation.

12. The optical standard according to claim 1, comprising a combination of at least one broadband-emitting emission standard module for the emission of at least one broad luminescence band and at least one narrow band-absorbing absorption module for the absorption of radiation in a narrow spectral region, wherein at least one narrow absorption band of the absorption module spectrally overlaps with at least one broad emission band of the emission standard module, further comprising at least one of a reducer module and of a diffuser module.

13. The optical standard of claim 12, further comprising a mirror module for partially or substantially totally reflecting the radiation.

14. The optical standard according to claim 1, wherein the optical standard modules are bonded or welded together by mechanical fixing means.

15. The optical standard of claim 14, wherein the optical standard modules are detachably joined together by clips or magnetic holders.

16. A kit, comprising a plurality of unlike layer-like optical standard modules, joinable together plane-parallel, which are suitable for entering into physical interaction with electromagnetic radiation striking one of their two principal surfaces and which in each instance differ from each other by at least one optical property, namely, by at least one of their absorption properties, emission properties, scatter properties and reflection properties, and the standard modules are selected from the group comprising:

emission standard modules for the emission of a luminescence spectrum, scatter modules for the wavelength-dependent or wavelength-independent diffuse scattering of the radiation, reducer modules for the substantially wavelength-independent reduction of radiation intensity with homogeneous transmission or transmission varying gradually or stepwise along its principal surfaces, optical filters for stopping out at least one defined wavelength-dependent spectral region, mirror modules, which partially or substantially totally reflect the radiation, and masks, which in at least one x, y direction running along their principal surfaces have sections of unlike optical properties, wherein the sections are arranged at least one x, y direction running along the module's principal surfaces and are selected from reflecting sections, totally absorbing sections, aperture sections, scatter sections, mirror sections and reducer sections, wherein the optical standard modules comprise at least one emission standard module for the emission of a luminescence spectrum and wherein the optical standard modules comprise a combination of a plurality of emission standard modules, which are adapted to each other so that their emission bands partially overlap each other.

17. A method for the spectral calibration or characterization of an optical measuring device comprising the steps of providing an optical standard comprising a combination of at least two layer-like optical standard modules having defined optical properties, joined together substantially plane-parallel, wherein the standard modules in each instance differ from each other by at least one optical property, namely, by at least one of their absorption properties, emission properties, scatter properties and reflection properties, and the standard modules are made so that they enter into physical interaction with electromagnetic radiation striking one of their two principal surfaces;

directing electromagnetic radiation on one of the two principal surfaces of one of the optical standard modules; and measuring an intensity of the electromagnetic radiation after physical interaction with the standard modules, wherein the optical standard modules comprise at least one emission standard module for the emission of a luminescence spectrum and wherein the optical standard modules comprise a combination of a plurality of emission standard modules, which are adapted to each other so that their emission bands partially overlap each other.

18. The method of claim 17, wherein the optical measuring device is selected from spectrally or integrally measuring luminescence-measuring systems, UV, UV/vis, IR and Raman spectrometers, microscopes and optical microtiter plate readout instruments.

* * * * *